United States Patent
Ueda et al.

(10) Patent No.: US 7,160,257 B2
(45) Date of Patent: Jan. 9, 2007

(54) HEALTH MANAGEMENT DEVICE FOR PREGNANT WOMAN

(75) Inventors: Yasuo Ueda, Sasayama (JP); Motoyoshi Maruo, Hyogo (JP); Yoshihiko Ashitaka, Ashiya (JP); Yuka Honda, Tokyo (JP)

(73) Assignee: Tanita Corporation, Tokyo (JP)

( * ) Notice: Subject to any disclaimer, the term of this patent is extended or adjusted under 35 U.S.C. 154(b) by 174 days.

(21) Appl. No.: 10/963,592

(22) Filed: Oct. 14, 2004

(65) Prior Publication Data

US 2005/0085742 A1 Apr. 21, 2005

(30) Foreign Application Priority Data

Oct. 16, 2003 (JP) ............................. 2003-356888
Jul. 27, 2004 (JP) ............................. 2004-218848

(51) Int. Cl.
*A61B 5/103* (2006.01)
*A61B 5/117* (2006.01)
*A61B 5/05* (2006.01)
*A61B 10/00* (2006.01)

(52) U.S. Cl. ...................... 600/587; 600/551; 600/547

(58) Field of Classification Search ................ 600/547, 600/587, 551
See application file for complete search history.

(56) References Cited

U.S. PATENT DOCUMENTS

| 5,449,000 | A  |   | 9/1995 | Libke et al. |
| 6,369,338 | B1 |   | 4/2002 | Kimura |
| 2002/0112898 | A1 | * | 8/2002 | Honda et al. ............... 177/245 |
| 2003/0023186 | A1 |   | 1/2003 | Ueda et al. |

FOREIGN PATENT DOCUMENTS

| EP | 1 080 687 A1 |   | 3/2001 |
| EP | 1 279 367 A1 |   | 1/2003 |
| JP | 2003-111741 | * | 4/2003 |

OTHER PUBLICATIONS

U.S. Appl. No. 10/855,531, filed May 28, 2004, Ueda et al.

* cited by examiner

*Primary Examiner*—Max F. Hindenburg
*Assistant Examiner*—Anurdha Roy
(74) *Attorney, Agent, or Firm*—McDermott Will & Emery LLP

(57) ABSTRACT

A health management device for pregnant women calculates the amount of change in body fat and the amount of change in total body water between a non-pregnant period and the time of measurement based on the amount of increase in body weight between the non-pregnant period and the time of measurement, and determines the health condition of a pregnant woman based on the calculated amount of change in body fat and amount of change in total body water.

9 Claims, 8 Drawing Sheets

| | | |
|---|---|---|
| DATE AND TIME OF MEASUREMENT: 6/1/2001  10:27 AM | | |
| GENDER/ BODY TYPE MODE | | STANDARD MALE |
| AGE | | 35 |
| BODY HEIGHT | | 168.0cm |
| BODY WEIGHT | | 63.4kg |
| IMPEDANCE | | 525Ω |
| FAT PERCENTAGE | | 26.2% |
| FAT MASS | | 16.6kg |
| FAT FREE MASS | | 46.8kg |
| TOTAL BODY WATER | | 34.2kg |
| BMI | | 23.9 |

| DATE AND TIME OF MEASUREMENT: 6/1/2001  10:27 AM ||
|---|---|
| GENDER/BODY TYPE MODE | MATERNITY |
| NUMBER OF WEEKS OF PREGNANCY | 24 WEEKS AND 5 DAYS |
| AGE | 35 |
| BODY HEIGHT | 159.0cm |
| BODY WEIGHT BEFORE AND AFTER CORRECTION | 52.0kg |
| BODY WEIGHT OF FETUS | 1.201kg |
| WEIGHT OF AMNIOTIC FLUID | 0.534kg |
| WEIGHT OF PLACENTA | 0.265kg |
| IMPEDANCE | 580Ω |
| BODY FAT PERCENTAGE | 21.3% |
| BODY FAT MASS | 11.1kg |
| FAT FREE MASS | 40.9kg |
| TOTAL BODY WATER | 29.9kg |
| BMI BEFORE CORRECTION | 21.4 |
| BODY WEIGHT IN NON-PREGNANT PERIOD | 49.0kg |
| BODY FAT MASS IN NON-PREGNANT PERIOD | 9.2kg |
| TOTAL BODY WATER IN NON-PREGNANT PERIOD | 28.0kg |
| AMOUNT OF INCREASE IN BODY WEIGHT FROM NON-PREGNANT PERIOD | 5.0kg |
| AMOUNT OF INCREASE IN BODY FAT FROM NON-PREGNANT PERIOD | 1.9kg |
| AMOUNT OF INCREASE IN BODY WATER FROM NON-PREGNANT PERIOD | 1.9kg |
| COMMENTS ON CURRENT HEALTH CONDITION ||
| YOUR CURRENT HEALTH CONDITION IS NORMAL. TRY TO KEEP THE CURRENT HEALTH CONDITION. ||

HEALTH MANAGEMENT DEVICE FOR PREGNANT WOMAN

BACKGROUND OF THE INVENTION (i) Field of the Invention

The present invention relates to a device which manages the health of a pregnant woman, particularly a device which manages the health of a pregnant woman with respect to edema and pregnancy toxemia.

(ii) Description of the Related Art

Heretofore, the occurrence of edema has been determined by pressing the crest of tibia with thumb and checking whether an impression is formed. Further, edema in pregnancy toxemia is generally seen in the legs, and when an increase of 500 g in body weight during the last one week is observed, one is determined to have mild pregnancy toxemia, and when edema is seen over the whole body, one is determined to have severe pregnancy toxemia.

However, determination of edema is liable to be influenced by the subjectivity of a doctor in charge of diagnosis, and quantitative determination thereof could not be made.

Further, it is known that an increase in body weight differs significantly depending on the amount of meals, the amount of excrement and the amount of sweat on a particular day and the body weight can be changed by about 500 g easily.

SUMMARY OF THE INVENTION

According to one aspect of the present invention, there is provided a health management device for pregnant women which comprises:
calculation means, and
determination means, wherein
the calculation means calculates the amount of change in body fat and the amount of change in total body water between a non-pregnant period and the time of measurement based on the amount of increase in body weight between the non-pregnant period and the time of measurement, and
the determination means determines the health condition of a pregnant woman based on the calculated amount of change in body fat and amount of change in total body water.

According to one embodiment of the present invention, in the health management device for pregnant women, the calculation means obtains the amount of change in body fat between the non-pregnant period and the time of measurement by multiplying the amount of increase in body weight between the non-pregnant period and the time of measurement by a first predetermined ratio and obtains the amount of change in total body water between the non-pregnant period and the time of measurement by multiplying the amount of increase in body weight between the non-pregnant period and the time of measurement by a second predetermined ratio. The first predetermined ratio is preferably about 58%, and/or the second predetermined ratio is preferably about 29%.

According to one embodiment of the present invention, the determination means determines the occurrence of edema or the occurrence of pregnancy toxemia.

According to one embodiment of the present invention, the health management device for pregnant women further comprises input means for inputting at least the current body weight and the body weight in the non-pregnant period as personal data of the pregnant woman, and the calculation means obtains the amount of increase in body weight between the non-pregnant period and the time of measurement by subtracting the body weight in the non-pregnant period from the current bodyweight. Preferably, the health management device for pregnant women further comprises impedance measuring means for measuring the bioelectrical impedance of the pregnant woman, and the calculation means calculates the current body fat mass and total body water by use of at least the current body weight input by the input means and the bioelectrical impedance measured by the impedance measuring means in accordance with a bioelectrical impedance analysis and also calculates a body fat mass and a total body water in the non-pregnant period by subtracting the amount of change in body fat and the amount of change in total body water from these current body fat mass and total body water, respectively.

According to one embodiment of the present invention, the health management device for pregnant women further comprises a memory for storing the amount of change in body fat and the amount of change in total body water which are calculated by the calculation means, and the determination means makes the determination based on transitions of changes in the amount of change in body fat and the amount of change in total body water which are stored in the memory.

According to one embodiment of the present invention, in the health management device for pregnant women, the determination means displays advice on the health of the pregnant woman.

The present invention is a health management device for pregnant women which comprises:
calculation means, and
determination means, wherein
the calculation means calculates the amount of change in body fat and the amount of change in total body water between a non-pregnant period and the time of measurement by, for example, multiplying the amount of increase in body weight between the non-pregnant period and the time of measurement by first and second predetermined ratios (preferably about 58% and about 29%), and
the determination means determines the health condition of a pregnant woman based on the calculated amount of change in body fat and amount of change in total body water. Thereby, the health of the pregnant woman with respect to edema and pregnancy toxemia can be managed objectively and quantitatively.

Further, the health management device for pregnant women according to the present invention further comprises input means for inputting at least the current body weight and the body weight in the non-pregnant period as personal data of the pregnant woman, and the calculation means obtains the amount of increase in body weight between the non-pregnant period and the time of measurement by subtracting the body weight in the non-pregnant period from the current body weight. Thus, the pregnant woman can use the device easily merely by remembering her body weight in the non-pregnant period. Further, when the health management device for pregnant women according to the present invention further comprises impedance measuring means for measuring the bioelectrical impedance of the pregnant woman and the calculation means calculates the current body fat mass and total body water by use of at least the current body weight input by the input means and the bioelectrical impedance measured by the impedance measuring means in accordance with a bioelectrical impedance analysis and also calculates a body fat mass and a total body water in the non-pregnant period by subtracting the amount of change in body fat and the amount of change in total body water from these current body fat mass and total body water, respectively, these data can still be obtained even if the pregnant woman does not remember them or they are not measured in the non-pregnant period, thereby making it possible to manage the health of the pregnant woman.

Further, the health management device for pregnant women according to the present invention further comprises a memory for storing the amount of change in body fat and the amount of change in total body water which are calculated by the calculation means, and the determination means makes the determination based on transitions of changes in the amount of change in body fat and the amount of change in total body water which are stored in the memory. Thereby, edema and/or pregnancy toxemia can be estimated before their occurrence based on the transitions.

Further, the health management device for pregnant women according to the present invention displays advice on the health of the pregnant woman, thereby making itself user-friendly to the pregnant woman.

DETAILED DESCRIPTION OF THE PREFERRED EMBODIMENTS

A health management device for pregnant women according to the present invention comprises calculation means and determination means. The calculation means calculates the amount of change in body fat and the amount of change in total body water between a non-pregnant period and the time of measurement by, for example, multiplying the amount of increase in body weight between the non-pregnant period and the time of measurement by first and second predetermined ratios (preferably about 58% and about 29%), and the determination means determines the health condition of a pregnant woman based on the calculated amount of change in body fat and amount of change in total body water.

The determination means determines the occurrence of edema.

The determination means determines the occurrence of pregnancy toxemia.

Further, the health management device for pregnant women according to the present invention further comprises input means for inputting at least the current body weight and the body weight in the non-pregnant period as personal data of the pregnant woman, and the calculation means obtains the amount of increase in body weight between the non-pregnant period and the time of measurement by subtracting the body weight in the non-pregnant period from the current bodyweight. The health management device for pregnant women according to the present invention further comprises impedance measuring means for measuring the bioelectrical impedance of the pregnant woman, and the calculation means calculates the current body fat mass and total body water by use of at least the current body weight input by the input means and the bioelectrical impedance measured by the impedance measuring means in accordance with a bioelectrical impedance analysis and also calculates a body fat mass and a total body water in the non-pregnant period by subtracting the amount of change in body fat and the amount of change in total body water from these current body fat mass and total body water, respectively.

Further, the health management device for pregnant women according to the present invention further comprises a memory for storing the amount of change in body fat and the amount of change in total body water which are calculated by the calculation means, and the determination means makes the determination based on transitions of changes in the amount of change in body fat and the amount of change in total body water which are stored in the memory.

Further, the determination means displays advice on the health of the pregnant woman.

EXAMPLE 1

Figure 1:
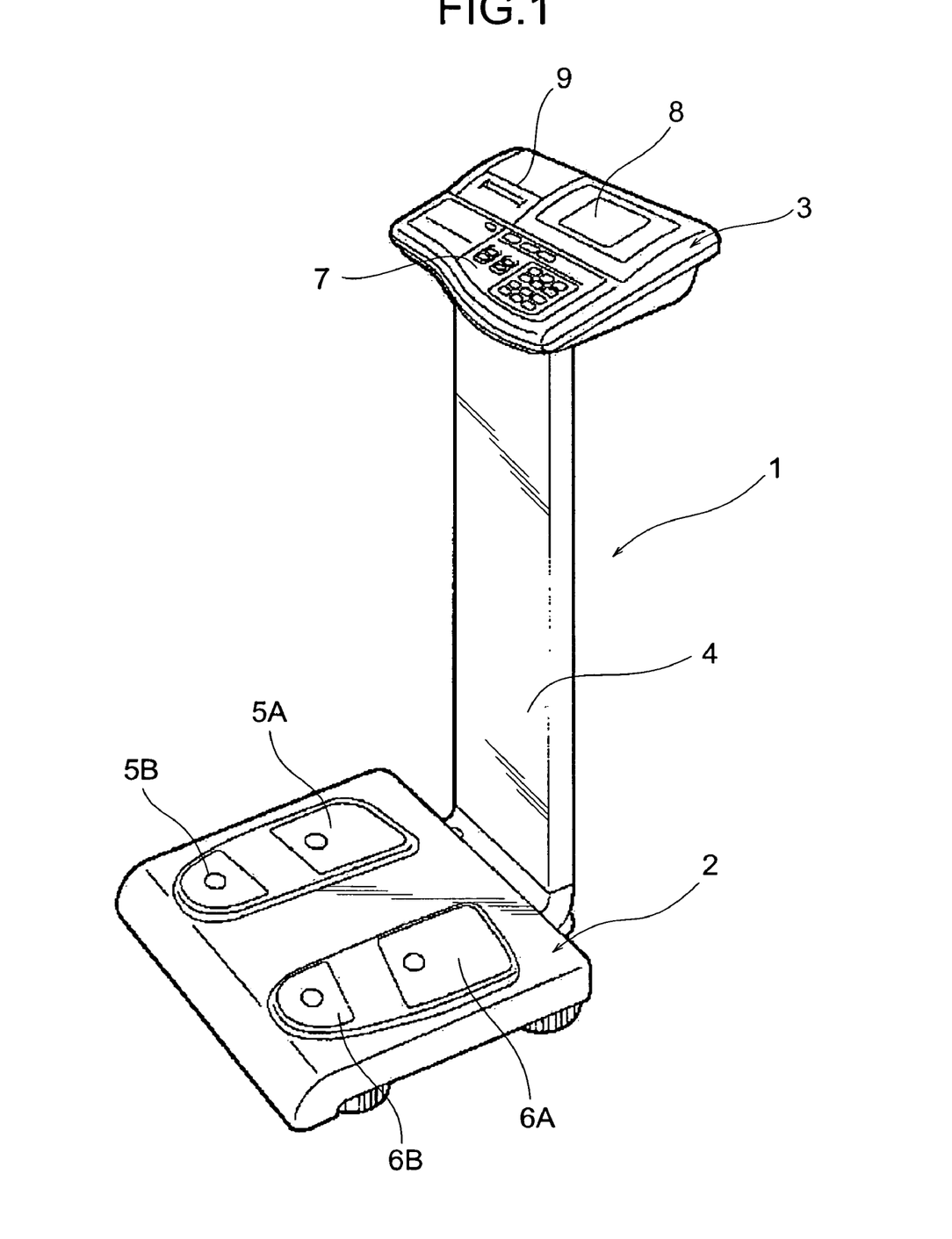
FIG. 1 is an external perspective view of an example of the present invention.

An example of the present invention will be described with reference to the drawings. FIG. 1 is an external perspective view of a health management device 1 for pregnant women according to the present invention. The device 1 roughly comprises a measuring section 2, a display/print section 3 and a support section 4 which is fixed to the not-shown base plate of the measuring section 2 and the display/print section 3. The measuring section 2 has the same constitution as that of a known body fat analyzer. The measuring section 2 incorporates a body weight measuring sensor, and a subject can measure her body weight by standing on the top surface of the measuring section 2. Further, on the top surface of the measuring section 2, current supplying electrodes 5A and 6A and voltage measuring electrodes 5B and 6B are provided to measure a bioelectrical impedance between both feet.

Figure 2:
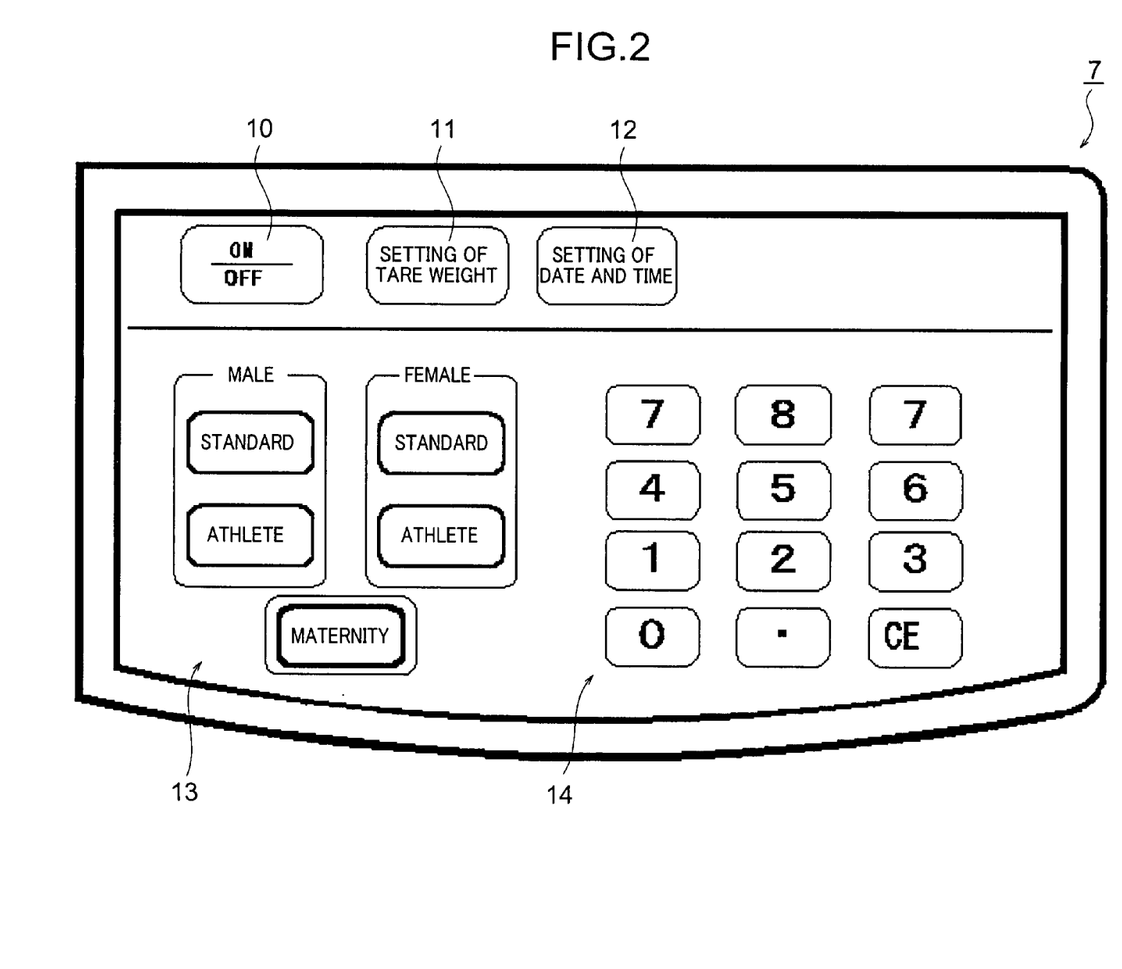
FIG. 2 is a diagram showing a display/print section of the example of the present invention.

Meanwhile, the display/print section 3 comprises an operation section 7 shown in FIG. 2, a display section 8 for displaying input data and results, and a print section 9 for printing the results of measurements.

The operation section 7 of FIG. 2 comprises a power switch 10, a tare weight setting key 11 for setting the weight of the tare of a subject, a key 12 for setting a date and a time, keys 13 for setting gender and a body type, and a numeric keypad 14 for setting data and the like.

Figure 3:
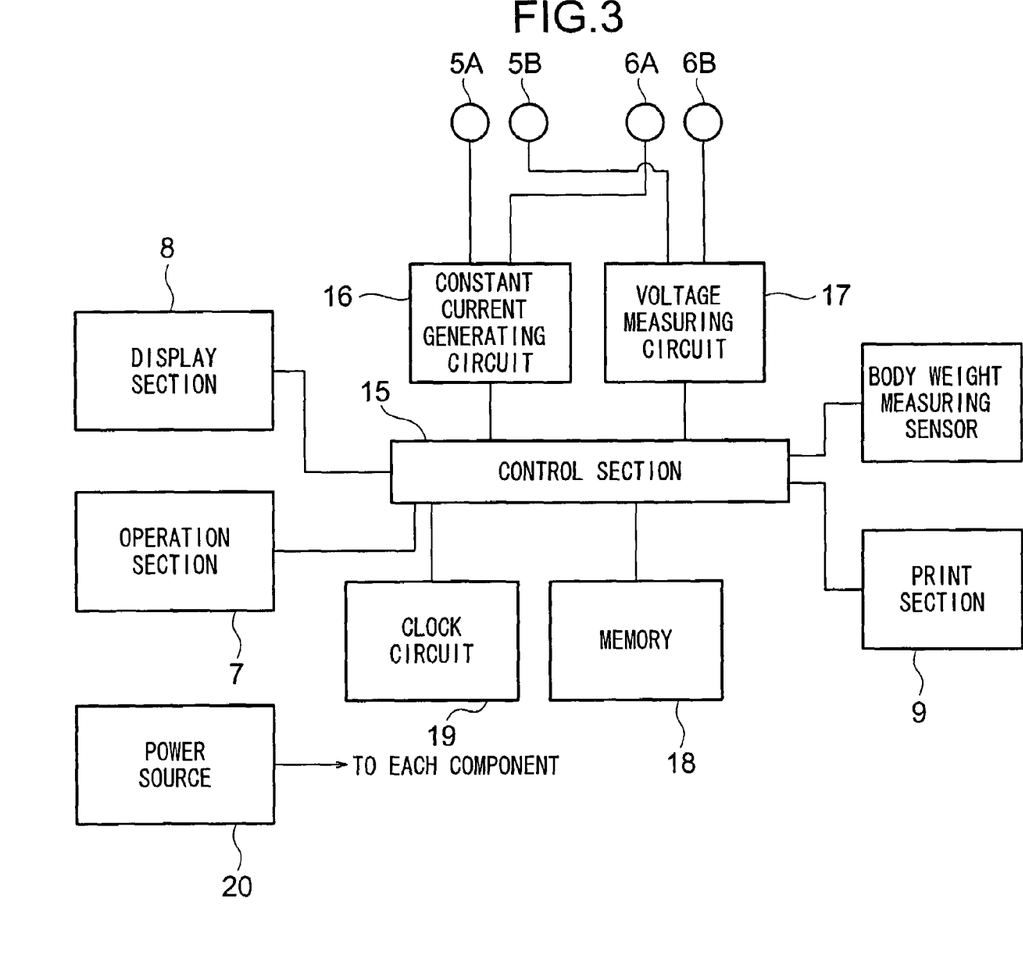
FIG. 3 is an electrical block diagram.

FIG. 3 is an electrical block diagram of the health management device 1 for pregnant women. The device 1 has a control section 15 incorporating a microcomputer. To the control section 15, the switch and keys of the operation section 7 of FIG. 2 are connected, and the display section 8 and the print section 9 are also connected. Further, from the measuring section 2, the current supplying electrodes 5A and 6A are connected to the control section 15 via a constant current generating circuit 16, and the voltage measuring electrodes 5B and 6B are connected to the control section 15 via a voltage measuring circuit 17. The body weight measuring sensor is also connected to the control section 15. In addition, to the control section 15, a memory 18 for storing data and a clock circuit 19 for generating date and time data such as the number of weeks of pregnancy are also connected. A power source 20 supplies electric power to these components.

Figure 4:
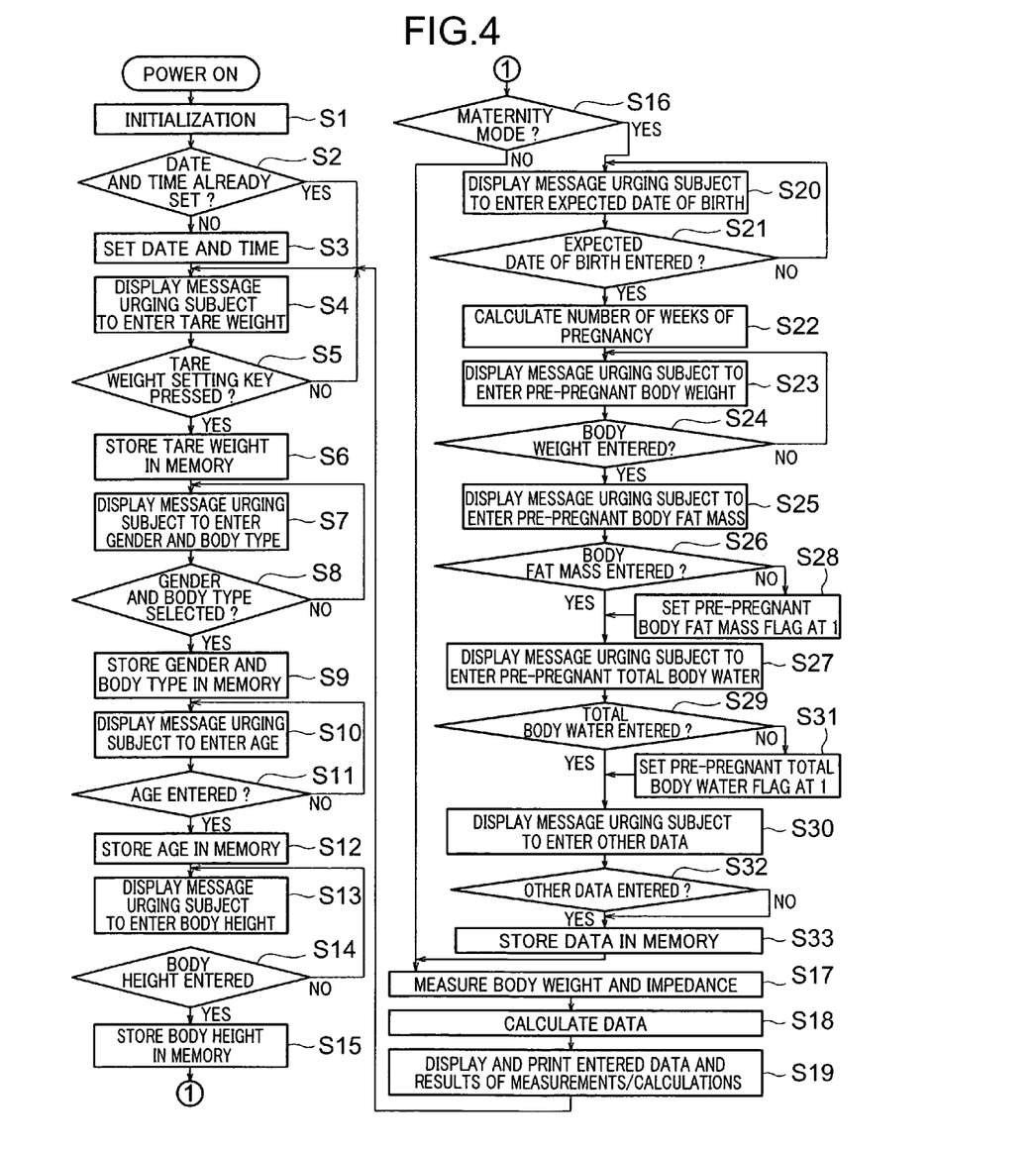
FIG. 4 is a flowchart of the example of the present invention.

Next, the operation of the health management device 1 for pregnant women according to the present invention will be described with reference to the flowchart of FIG. 4. Firstly, when the power switch 10 is pressed, the control section 15 initializes the microcomputer, the memory 18 and the like in STEP S1. At that time, measurement data and setting data of the past such as input data, measurement data and calculation result data in a non-pregnant period (before pregnancy) are kept intact. Then, in STEP S2, the control section 15 determines whether a date and a time are already set. If the date and time are already set, the control section 15 proceeds to STEP S4. If the date and time are not set yet, the control section 15 sets the date and time in STEP S3. A detailed description of the setting of the date and time is omitted since it is the same as that used in general apparatuses.

In STEP S4, the control section 15 displays a message "Please enter the weight of your clothing or tare using the numeric keypad 14 and then press the tare weight setting key 11." in the display section 8. Then, when a subject enters 1.0 kg by use of the numeric keypad 14 and presses the tare weight setting key 11, it is determined to be "Yes" in STEP S5, and the control section 15 proceeds to STEP S6 and stores the tare weight in the memory 18. If the tare weight setting key 11 is not pressed in STEP S5, the control section 15 returns to STEP S4 and repeats displaying the message which urges the subject to enter the tare weight.

Then, in STEP S7, the control section 15 displays in the display section 8 a message which urges the subject to press a key which matches the subject among the keys 13 for setting gender and a body type. For example, when the subject is a standard male, he presses a "standard" key in the frame named "male" of FIG. 2. Then, the control section 15 determines in STEP S8 that the key has been pressed and proceeds to STEP S9 so as to store data of the pressed key in the memory 18. Until it is confirmed in STEP S8 that the key has been pressed, the control section 15 keeps returning to STEP S7 and displaying the message urging the subject to press the key. Similarly, in STEPS S10 to S12, the control section 15 urges the subject to enter his age, the subject enters his age, and the control section 15 stores the age data in the memory 18. In STEPS S13 to S15, the control section 15 urges the subject to enter his body height, the subject enters his body height, and the control section 15 stores the body height data in the memory 18.

Then, in STEP S16, it is determined which key has been pressed in STEP S8. In this case, since the subject is a standard male, it is determined to be "No", and the control section 15 proceeds to STEP S17. In STEP S17, measurements are started after it is confirmed that the subject stands on the measuring section 2 with his toes in contact with the current supplying electrodes 5A and 6A and his heels in contact with the voltage measuring electrodes 5B and 6B. To measure a body weight, an output from the body weight sensor is taken into the control section 15, and the body weight is calculated in STEP S18. Meanwhile, to measure an impedance, a constant electric current is passed between the electrodes 5A and 6A from the constant current generating circuit 16, a voltage between the electrodes 5B and 6B is measured by the voltage measuring circuit 17, and the impedance is calculated from the relationship between the current and the voltage in STEP S18. In STEP S18, the tare weight is subtracted from the measured body weight so as to determine the body weight of the subject; a body fat percentage is calculated from the impedance; a body fat mass is calculated by multiplying the body weight by the body fat percentage; a fat free mass is calculated by subtracting the body fat mass from the body weight; a total body water is calculated by multiplying the fat free mass by an average body water percentage which is 73.2%; and BMI (Body Mass Index) is calculated from the body height and the body weight. Then, the results of the calculations are not only displayed in the display section 8 but also printed out from the print section 9 in STEP S19.

Figure 5:
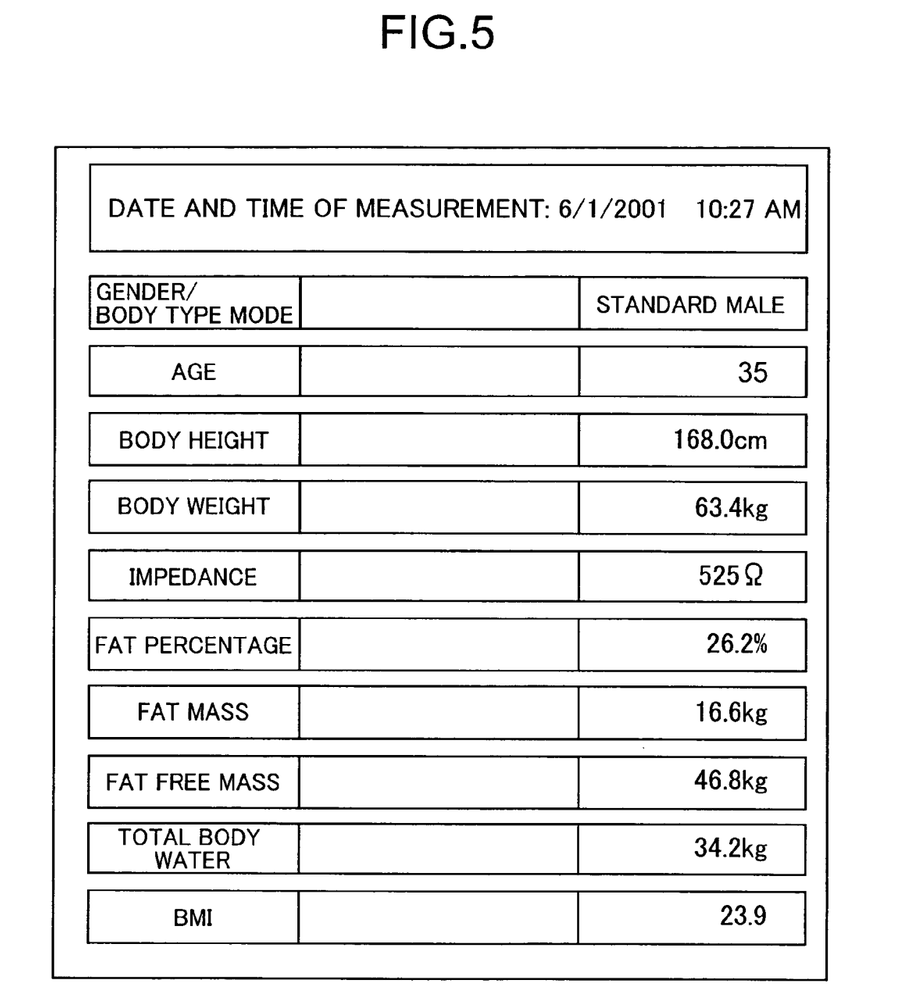
FIG. 5 is a diagram showing an example of printout in a non-maternity mode.

FIG. 5 is an example of the printout. In addition to the date and time of the measurements, the entered personal data such as gender, a body type, age and a body height and the results of the measurements and calculations carried out in STEPS S17 and S18 are printed out.

After displaying and printing out the data, the control section 15 returns to STEP S4 and waits for the next input data.

If a "maternity" key has been pressed in the above STEP S8, it is determined to be "Yes" in STEP S16, and the control section 15 proceeds to STEP S20. In STEP S20, the control section 15 displays in the display section 8 a message which urges the subject to enter an expected date of birth. STEPS S20 and S21 are repeated until the date is entered from the numerical keypad in STEP S21. Once the expected date of birth is entered, it is determined to be "Yes" in STEP S21, and the control section 15 calculates the number of weeks of pregnancy from the entered expected date of birth and the date of measurements in STEP S22 and then proceeds to STEP S23 where the control section 15 displays a message urging the subject to enter her body weight before pregnancy (in a non-pregnant period). Then, the control section 15 proceeds to STEP S24.

STEPS S23 and S24 are repeated until the body weight in the non-pregnant period is entered from the numerical keypad in STEP S24. Once the body weight value is entered, it is determined to be "Yes" in STEP S24, and the control section 15 proceeds to STEP S25 where the control section 15 displays a message urging the subject to enter her body fat mass before pregnancy (in the non-pregnant period). Once the body fat mass is entered from the numerical keypad, it is determined to be "Yes" in STEP S26, and the control section 15 proceeds to STEP S27. At that time, if the body fat mass in the non-pregnant period is not entered within a given time, it is determined to be "No" in STEP S26, and the control section 15 sets a non-pregnant period body fat mass flag in the memory 18 at "1" in STEP S28 and proceeds to STEP S27.

In STEP S27, the control section 15 displays a message urging the subject to enter her total body water before pregnancy (in the non-pregnant period). Once the total body water is entered from the numerical keypad, it is determined to be "Yes" in STEP S29, and the control section 15 proceeds to STEP S30. At that time, if the total body water in the non-pregnant period is not entered within a given time, it is determined to be "No" in STEP S29, and the control section 15 sets a non-pregnant period total body water flag in the memory 18 at "1" in STEP S31 and proceeds to STEP S30. In STEP S30, the control section 15 displays a message urging the subject to enter her data about edema and pregnancy toxemia. Once the data are entered from the numerical keypad, it is determined to be "Yes" in STEP S32, and the control section 15 stores these entered data and the states of the flags in the memory 18 in STEP S33. The data entered in STEP S32 include blood pressure values in the expansion and contraction stages which are associated with determination of pregnancy toxemia, data about proteinuria obtained by examining twenty-four-hour urine in accordance with an Enbach method or a measurement method based on the Enbach method, and data about whether edema is seen only in a portion of the body of the pregnant woman or on her whole body. If no data is entered in STEP S32, the control section 15 proceeds to STEP S33.

The control section 15 stores the data entered in STEP S20 and the subsequent steps in the memory 18 in STEP S33 and then proceeds to STEP S17.

In the "maternity" mode, processing in STEP S17 is the same as that in the non-maternity mode. However, in the "maternity" mode, the following data calculations are also performed in addition to data calculations in STEP S18 in the non-maternity mode.

Figure 6:
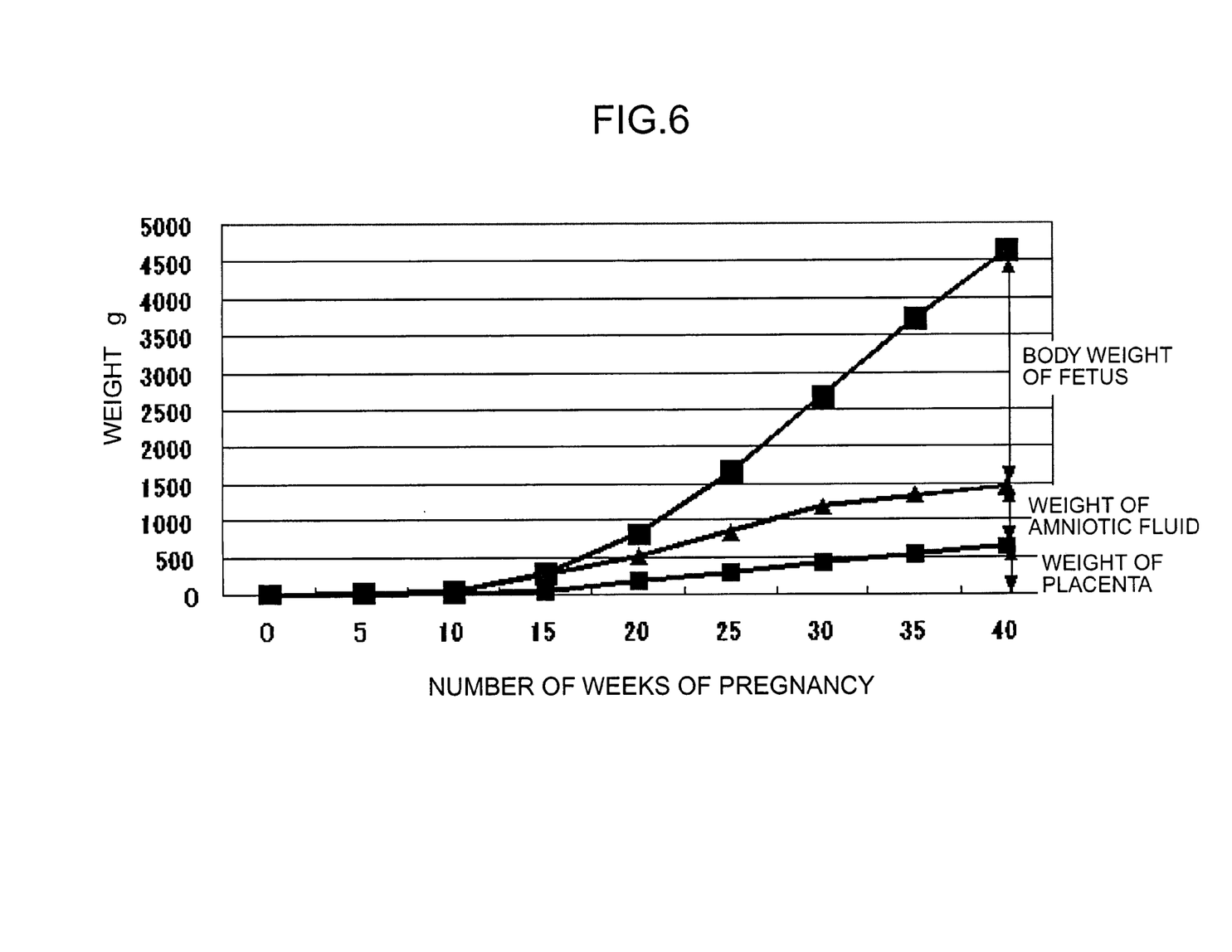
FIG. 6 is a diagram showing the relationship between the number of weeks of pregnancy and the weight of fetal portion.

The body weight of fetus, the weight of amniotic fluid and the weight of placenta which correspond to the number of weeks of pregnancy are read from the graphs (whose data are stored in the memory 18) shown in FIG. 6. They are subtracted from the measured body weight from which the tare weight has already been subtracted so as to determine a body weight excluding the weight of the fetal portion. Based on the body weight, a body fat percentage, a body fat mass, a fat free mass, a total body water and the ratio of the total body water to the body fat mass (TBW/FAT) at the time of the measurement are calculated.

Then, the body weight in the non-pregnant period which has been input in STEP S24 is subtracted from the current body weight measured in STEP S17 so as to determine the amount of increase in the body weight between the non-pregnant period and the time of the measurement. Further, the amount of increase in body fat mass and the amount of increase in total body water between the non-pregnant period and the time of the measurement are determined by subtracting the body fat mass and the total body water in the non-pregnant period which have been entered in STEPS S26 and S29 from the current body fat mass and total body water calculated in STEP S18 by use of data such as the body weight and impedance measured in STEP S17 in accordance with a bioelectrical impedance method. However, in general, few pregnant women remember data in a non-pregnant period such as a body weight, a body fat mass and a total body water, and they can remember only body weights or comparable data at best.

Meanwhile, the present inventor has found that the ratios of the amount of change in body fat and the amount of change in total body water between a non-pregnant period and the time of measurement to the amount of increase in body weight between the non-pregnant period and the time of measurement are about 58% and about 29%, respectively.

For example, when a body weight in a non-pregnant period is 50 kg and a body weight at the time of measurement is 55 kg, the amount of increase in the body weight is 5 kg. By multiplying the 5 kg by 58% and 29%, the amount of change in body fat and the amount of change in total body water between the non-pregnant period and the time of measurement are determined to be 2.9 kg and 1.45 kg, respectively. Then, by subtracting these values from a body fat mass and a total body water at the time of measurement, a body fat mass and a total body water in the non-pregnant period are determined.

The present inventor has found that these ratios remain unchanged from the $6^{th}$ week to the $16^{th}$ week of pregnancy and do not change even if the body weight changes due to morning sickness or some other reasons. Therefore, when the measurement is made at least once between the $6^{th}$ week and the $16^{th}$ week of pregnancy, it is determined whether the flag(s) set in STEP S28 and/or STEP S31 are/is 1. When the flag(s) is/are 1, the amount of increase in body weight between the non-pregnant period and the present time is multiplied by the ratio(s) so as to determine the amount of change in body fat and/or the amount of change in total body water between the non-pregnant period and the time of the measurement, and the amount of change in body fat and the amount of change in total body water are subtracted from the current body fat mass and total body water so as to determine a body fat mass and a total body water in the non-pregnant period in STEP S18.

The amount of change in body fat and the amount of change in total body water between the non-pregnant period and the time of the measurement can be calculated even in the middle or late stage of pregnancy, if a body fat mass and a total body water in the non-pregnant period which are determined by making a measurement at least once between the $6^{th}$ week and the $16^{th}$ week of pregnancy are stored in the memory 18.

Figure 7:
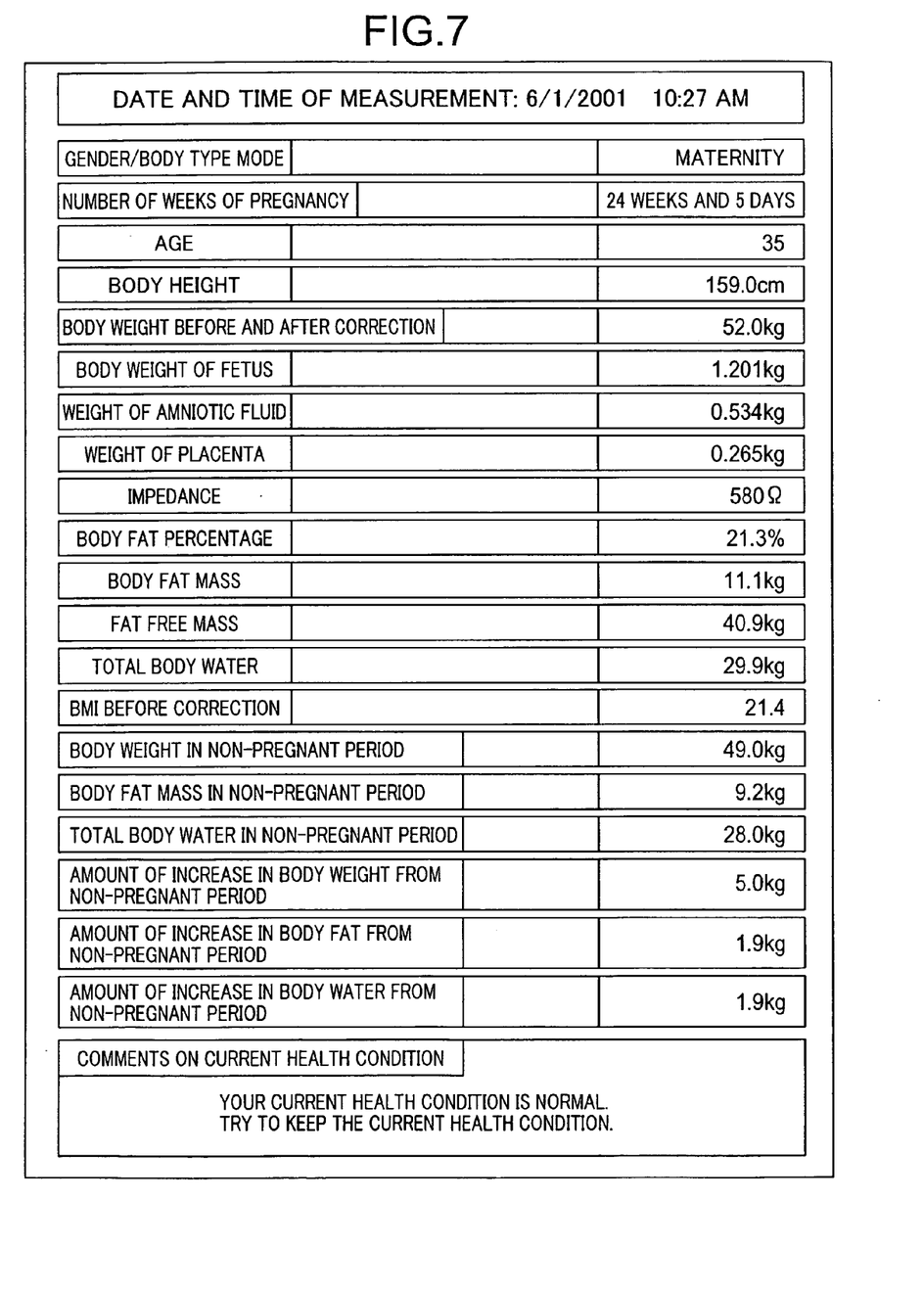
FIG. 7 is a diagram showing an example of printout in a maternity mode.

Then, the results are not only stored in the memory 18 but also displayed in the display section 8 and printed out in the print section 9 in STEP S19. An example of printout of the results of measurements made on 24 weeks of pregnancy plus 5 days in FIG. 7 is different from the example of FIG. 5 in that it additionally shows the number of weeks of pregnancy, a pre-correction body weight (from which a tare weight has been subtracted) including the weight of fetal portion and a post-correction body weight excluding the weight of the fetal portion, the weight of fetus, the weight of amniotic fluid, the weight of placenta, pre-correction BMI determined from the body weight (from which the tare weight has been subtracted) including the weight of the fetal portion and a body height, a pre-pregnant body weight, a pre-pregnant body fat mass, a pre-pregnant total body water, the amount of increase in body weight and the amounts of changes in body fat and body water between the prepregnant period and the time of measurement, and a comment (to be described later) on the current health condition. The pre-correction BMI is calculated and displayed or printed because the data is provided to a gynecologist who determines the status of the growth of a fetus from the value of the pre-correction BMI.

Further, similarly, for the purpose of data provision, pre-pregnant BMI may also be printed or displayed in addition to the example of printout shown in FIG. 7 or data displayed in the display section 8.

After completion of STEP S19 where the obtained results are displayed and printed, the control section 15 returns to STEP S4 and waits for the next input data.

Figure 8:
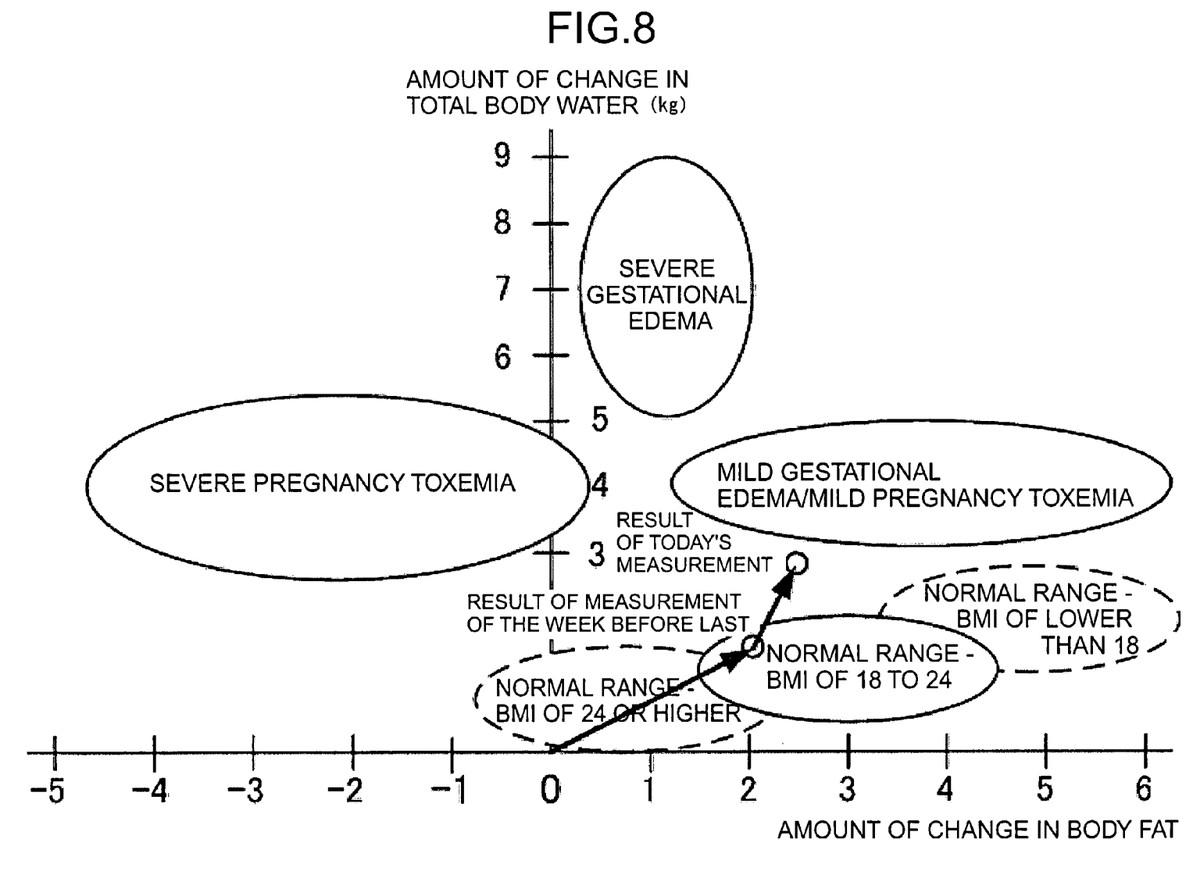
FIG. 8 is a diagram showing the relationship between the amount of change in body fat and the amount of change in total body water.

The above comment on the health condition is primarily determined by the graph of the amount of change in body fat and the amount of change in total body water between the non-pregnant period and the present time as shown in FIG. 8. The data of the graph used for the determination is stored in the memory 18. When the current amount of increase in body fat and amount of change in total body water are calculated in STEP S18, the current position is determined from the graph, and a comment such as "You may be losing a balance between fat and water. Be careful not to be overweight.", "When the body weight or body fat increases in the middle stage of pregnancy, you will have severe edema or an increase in blood pressure, increasing the possibility of becoming toxemia, in the late stage of pregnancy.", "The water content of your body is too high. Aren't your hands and feet swollen? Are you calculating calories you take? Aren't you taking spicy food or water excessively?" or "The balance between fat and water in your body is not good. You may be having toxemia. Pay careful attention to the results of examination." is read from the memory 18 and displayed and/or printed.

The graph in FIG. 8 is drawn by setting the non-pregnant period or immediate aftermath of pregnancy as the origin (where amounts of changes are 0) and plotting changes in the body fat mass and the total body water between the non-pregnant period and the time of measurement, and the occurrence of edema or toxemia is determined by the position. In the graph in FIG. 8, since the normal range, the ranges of toxemia and the ranges of edema vary depending on a body type, e.g., a BMI in the non-pregnant period of lower than 18, 18 to 24, or 24 or higher, and the number of weeks of pregnancy, the graph is stored in the memory 18 for each body type and each group of the number of weeks of pregnancy. For example, when the body type is classified into three types and the number of weeks of pregnancy is divided into three groups (early stage of pregnancy: 0 to $15^{th}$ week, middle stage: $16^{th}$ week to $27^{th}$ week, late stage: $28^{th}$ week or later), 9 different types of graphs are stored in the memory 18. FIG. 8 shows the determination ranges for a BMI of 18 to 24 and the middle stage of pregnancy ($16^{th}$ week to $27^{th}$ week). To understand these determination ranges, the normal ranges for other body types are also shown by broken lines for reference.

It is also possible that the condition at the time of measurement is plotted from the origin (data in the non-pregnant period) in the graph of FIG. 8 along with an increase in the number of weeks of pregnancy, the positions of the plotted points and the direction of movement of the plotted points are determined in the controller 15 by use of analysis software and a comment on the health condition is displayed or printed. At that time, to increase the accuracy of determination of the health condition, the number of measurements is preferably large.

FIG. 8 shows the results of measuring a pregnant woman in the $20^{th}$ week of pregnancy who shows a BMI of 18 to 24. Although the measured amount of change in body fat and amount of change in total body water are out of the normal range as 2.5 kg and 3.0 kg, respectively, they were within the normal range in the week before last ($18^{th}$ week). However, since the direction of movement from the week before last to the date of the measurement is pointed toward the range of mild gestational edema/mild pregnancy toxemia, it is expected that the subject may have mild gestational edema or mild pregnancy toxemia. Consequently, a comment informing the subject of the possibility of having mild gestational edema or mild pregnancy toxemia is displayed or printed in STEP S19 in FIG. 4.

Further, in the above example, the total body water and the body fat mass are calculated by use of the corrected body weight excluding the weight of the fetal portion. However, the calculations of the total body water and the body fat mass are not limited thereto, and it has been found that the results of the calculations show similar tendency even if the calculations are performed by using the measured body weight directly. Accordingly, the pre-correction body weight may be used to perform the calculations.

What is claimed is:

1. A health management device for pregnant women which comprises calculation means and determination means;
   wherein the calculation means calculates the amount of change in body fat and the amount of change in total body water between a non-pregnant period and the time of measurement based on the amount of increase in body weight between the non-pregnant period and the time of measurement;
   wherein the determination means determines the health condition of a pregnant woman based on the calculated amount of change in body fat and amount of change in total body water;
   wherein the calculation means obtains the amount of change in body fat between the non-pregnant period and the time of measurement by multiplying the amount of increase in body weight between the non-pregnant period and the time of measurement by a first predetermined ratio and obtains the amount of change in total body water between the non-pregnant period and the time of measurement by multiplying the amount of increase in body weight between the non-pregnant period and the time of measurement by a second predetermined ratio; and
   wherein the first predetermined ratio is about 58%.

2. A health management device for pregnant women which comprises calculation means and determination means;
   wherein the calculation means calculates the amount of change in body fat and the amount of change in total body water between a non-pregnant period and the time of measurement based on the amount of increase in body weight between the non-pregnant period and the time of measurement;
   wherein the determination means determines the health condition of a pregnant woman based on the calculated amount of change in body fat and amount of change in total body water;
   wherein the calculation means obtains the amount of change in body fat between the non-pregnant period and the time of measurement by multiplying the amount of increase in body weight between the non-pregnant period and the time of measurement by a first predetermined ratio and obtains the amount of change in total body water between the non-pregnant period and the time of measurement by multiplying the amount of increase in body weight between the non-pregnant period and the time of measurement by a second predetermined ratio; and
   wherein the second predetermined ratio is about 29%.

3. A health management device for pregnant women which comprises calculation means and determination means;
   wherein the calculation means calculates the amount of change in body fat and the amount of change in total body water between a non-pregnant period and the time of measurement based on the amount of increase in body weight between the non-pregnant period and the time of measurement;
   wherein the determination means determines the health condition of a pregnant woman based on the calculated amount of change in body fat and amount of change in total body water;
   wherein the calculation means obtains the amount of change in body fat between the non-pregnant period and the time of measurement by multiplying the amount of increase in body weight between the non-pregnant period and the time of measurement by a first predetermined ratio and obtains the amount of change in total body water between the non-pregnant period and the time of measurement by multiplying the amount of increase in body weight between the non-pregnant period and the time of measurement by a second predetermined ratio; and wherein the first predetermined ratio is about 58%, and the second predetermined ratio is about 29%.

4. The device according to any one of claims 1 to 3, wherein the determination means determines the occurrence of edema.

5. The device according to any one of claims 1 to 3, wherein the determination means determines the occurrence of pregnancy toxemia.

6. The device according to any one of claims 1 to 3, further comprising input means, wherein the input means inputs at least the current body weight and the body weight in the non-pregnant period as personal data of the pregnant woman, and the calculation means obtains the amount of increase in body weight between the non-pregnant period and the time of measurement by subtracting the body weight in the non-pregnant period from the current body weight.

7. The device according to claim 6, further comprising impedance measuring means, wherein the impedance measuring means measures the bioelectrical impedance of the pregnant woman, and the calculation means calculates the current body fat mass and total body water by use of at least the current body weight input by the input means and the bioelectrical impedance measured by the impedance measuring means in accordance with a bioelectrical impedance analysis and also calculates a body fat mass and a total body water in the non-pregnant period by subtracting the amount of change in body fat and the amount of change in total body water from these current body fat mass and total body water, respectively.

8. The device according to any one of claims 1 to 3, further comprising a memory, wherein the memory stores the amount of change in body fat and the amount of change in total body water which are calculated by the calculation means, and the determination means makes the determination based on transitions of changes in the amount of change in body fat and the amount of change in total body water which are stored in the memory.

9. The device according to any one of claims 1 to 3, wherein the determination means displays advice on the health of the pregnant woman.

* * * * *